(12) United States Patent
Schleck et al.

(10) Patent No.: US 6,677,381 B1
(45) Date of Patent: Jan. 13, 2004

(54) GUAIFENESIN TANNATE

(75) Inventors: James R. Schleck, Somerset, NJ (US); Vilas M. Chopdekar, Edison, NJ (US)

(73) Assignee: Jame Fine Chemicals, Inc., Bound Brook, NJ (US)

(*) Notice: Subject to any disclaimer, the term of this patent is extended or adjusted under 35 U.S.C. 154(b) by 0 days.

(21) Appl. No.: 10/017,131

(22) Filed: Dec. 14, 2001

(51) Int. Cl.$^7$ .................... A61K 31/135; A01N 25/00; C07C 69/88
(52) U.S. Cl. ................ 514/653; 514/646; 514/849; 560/68
(58) Field of Search ................... 560/68; 514/849, 514/646, 653

(56) References Cited

U.S. PATENT DOCUMENTS

| | | | |
|---|---|---|---|
| 5,599,846 A | 2/1997 | Chopdekar et al. | 514/653 |
| 5,663,415 A | 9/1997 | Chopdekar et al. | 560/68 |
| 6,037,358 A | 3/2000 | Gordziel | 514/357 |
| 6,287,597 B1 | 9/2001 | Gordziel | 424/464 |
| 6,306,904 B1 | 10/2001 | Gordziel | 514/530 |
| 6,509,492 B1 | 1/2003 | Venkataraman | 580/68 |

*Primary Examiner*—Alan L. Rotman
*Assistant Examiner*—Taylor V Oh
(74) *Attorney, Agent, or Firm*—Jack Matalon

(57) ABSTRACT

The invention pertains to a novel composition comprising guaifenesin tannate and to a method for preparing guaifenesin tannate by reacting guaifenesin with tannic acid at a temperature above the melting point of guaifenesin. The guaifenesin tannate has extended release properties and is useful in pharmaceutical compositions as an expectorant in warm-blooded animals or as a muscle relaxant in non-human animals.

10 Claims, No Drawings

GUAIFENESIN TANNATE

FIELD OF THE INVENTION

The invention pertains to guaifenesin tannate and its method of preparation as well as pharmaceutical compositions containing guaifenesin tannate.

BACKGROUND OF THE INVENTION

Guaifenesin is a well-known commercially available compound. It is frequently referred to as guaiphenesin or glyceryl guiacolate. Its chemical name is 3-(2-methoxyphenoxy)-1,2-propanediol. It is a solid having a melting point of 78.5° C., and its molecular formula is $C_{10}H_{14}O_4$. It is only slightly soluble (i.e, about 5 wt. %) in water, but is readily soluble in alcohols such as methanol, ethanol, isopropanol, etc. By way of further identification, its CAS number is 93-14-1.

Guaifenesin finds its principal use as an expectorant for promoting or facilitating the removal of secretions from the respiratory tract in a warm-blooded animal, principally a human being. It helps to loosen phlegm (mucus) and thin bronchial secretions to rid the bronchial passageways of bothersome mucus, drain bronchial tubes and makes coughs more productive. It is typically administered to human beings in need of such medication in the form of tablets and/or suspensions.

Guaifenesin has also proven useful as a central nervous system muscle relaxant for non-human warm-blooded animals, particularly horses and cattle. For animals in need of a muscle relaxant, guaifenesin is typically administered in injectable form.

In recent years, research has indicated that guaifenesin may be useful for alleviation of the symptoms of fibromyalgia syndrome and chronic fatigue syndrome. If such research proves that guaifenesin does in fact alleviate the symptoms of FMS and CFS, it will be a very welcome adjunct in the treatment of these syndromes which are quite painful.

In contradistinction to the antihistamines of which many are unstable in the form of their free bases, guaifenesin is relatively stable. Therefore, little, if any attention, has been paid in recent years to improving guaifenesin compositions. On the other hand, there is a considerable amount of prior art which has emerged in recent years which has been directed to salts of antihistamines, principally tannate salts, which stabilize the antihistamine bases. For example, see U.S. Pat. Nos. 5,599,846; 5,663,415; 6,037,358; 6,287,597; and 6,306,904.

Tannic acid is commercially available and is used in many industrial applications. It is frequently referred to as gallotannic acid, gallotannin; glycerite or tannin. It is a pale tan powder having a decomposition point of 210–215° C., and is highly soluble in water and alcohols. Its molecular formula is $C_{76}H_{52}O_{46}$; its CAS number is 1401-55-4. Tannic acid is typically produced from Turkish or Chinese nutgall and has a complex non-uniform chemistry and typically contains about 5–10 wt. % water.

As mentioned above, guaifenesin, in contradistinction to the antihistamines, is quite stable and therefor would not require the addition of a material such as tannic acid to render it stable. However, guaifenesin does have one drawback: it is readily absorbed in the patient's body, but its action is relatively short-lived. Indeed, its plasma half-life is only one hour. Accordingly, while it provides relatively quick relief to the patient, the patient is required to take relatively high doses several times a day until the condition which necessitated the administration of the guaifenesin has been alleviated. This presents a particular problem to the patient suffering from chronic bronchitis who is therefore required to be on a constant regimen of guaifenesin, thereby increasing the likelihood of the occurrence of undesirable side effects.

It would be very desirable if a form of guaifenesin was available which would have extended-release properties, i.e., the guaifenesin would be slowly released into the patient's bloodstream over a prolonged period of time. Thus far, the only slow-release forms of guaifenesin which are available are those such as polymer coated tablets. Such prior art formulations provide mixed results in that the guaifenesin is not available for adsorption into the patient's bloodstream until the polymeric coating has been dissolved, but thereafter the guaifenesin is quickly absorbed and metabolized. The result is that frequently, the guaifenesin must again be administered to the patient within the period of only a few hours.

DETAILED DESCRIPTION OF THE INVENTION

It has now been found that it is possible to provide an extended-release form of guaifenesin by reacting it with tannic acid so as to form a novel composition hereinafter referred to as guaifenesin tannate.

The guaifenesin tannate is prepared by a method involving the following steps:

(a) heating guaifenesin to a temperature above its melting point; and (b) slowly (e.g., over a period of 5–30 minutes) adding tannic acid to the molten guaifenesin, while agitating the reaction mixture.

It is not necessary to have any water or other diluent present during the reaction between the guaifenesin and the tannic acid (indeed, tannic acid itself contains about 5–10 wt. % water). Step (b) is carried out while the guaifenesin is maintained at a temperature in the range of about 80 to about 100° C., preferably 85 to 95° C. After the tannic acid has been added, the reaction mixture is agitated for an additional period of time (10 minutes–2 hours) while maintaining the temperature in the range of about 80 to about 100° C. and the reaction mass is thereafter cooled to room temperature. The solid reaction mass comprising the guaifenesin tannate is preferably thereafter milled to form a free-flowing powder preferably to a particle size of about 50 to about 200 mesh. The molar ratio of the guaifenesin to the tannic acid is in the range of about 3 to about 10, preferably, 4 to 7, moles of guaifenesin per mole of tannic acid. It has been found that using less than 3 moles of guaifenesin per mole of tannic acid results in an incomplete reaction, while the use of more than 10 moles of guaifenesin per mole of tannic acid results in a sticky, hygroscopic reaction mass which is difficult to convert into a free-flowing powder.

It would have been expected that the guaifenesin tannate product resulting from the two step method described above would have the structure of an ester since the reaction involves an alcohol, i.e., guaifenesin which is a diol, and an acid, i.e., tannic acid. It is well known that in the course of a typical esterification reaction, water is formed as a by-product. However, it was found that in the course of the reaction between the guaifenesin and the tannic acid, water was not produced as a by-product. Accordingly, it is believed that the guaifenesin tannate is a complex.

The guaifenesin tannate of the invention has the following physical properties: It has a softening point in the range of 57 to 62° C., in contradistinction to the melting point of 78.5° C. for guaifenesin and 210–215° C. decomposition point for tannic acid.

The guaifenesin tannate of the invention is a light-tan colored powder which is soluble in water and alcohols, but is insoluble in methylene chloride, chloroform or toluene. In contradistinction thereto, guaifenesin is a white powder which is soluble in water, alcohols and methylene chloride and sparingly soluble in toluene, while tannic acid is a tan-colored powder which is soluble in water and alcohols, but is insoluble in methylene chloride, chloroform or toluene. Further proof that the guaifenesin tannate of the present invention is a new material and not a physical mixture of guaifenesin and tannic acid has been obtained by the use of FTIR spectroscopy which is discussed in respect to Examples 1–3 below.

The guaifenesin tannate of the invention may be prepared for oral administration in the form of powders, capsules, elixirs, syrups, etc. Preferably the compositions are prepared in the form of tablets containing about 100 to about 500 mg of guaifenesin tannate of the invention per tablet or as a suspension, i.e., liquid, wherein each 5 ml (teaspoon) of liquid would contain about 100 to about 400 mg of the guaifenesin tannate of the invention.

Tablets containing the unique guaifenesin tannate composition of the invention may be prepared in a conventional manner by the addition of suitable pharmaceutical carriers, including fillers, diluents, lubricants and the like as well as conventional and well known binding and disintegrating agents. A typical tablet composition of the present invention will contain, in addition to the guaifenesin tannate, microcrystalline cellulose, corn starch, magnesium stearate, croscarmellose sodium and coloring matter.

The suspension formulations of the guaifenesin tannate of the present invention will typically additionally contain citric acid, caramel, glycerin, sorbitol solution, propylene glycol, saccharin sodium, sodium benzoate, flavoring agent and purified water.

When intended for use as a muscle relaxant for non-human animals such as horses and cattle, the guaifenesin tannate of the invention will be administered in injectable form containing about 50 to about 200 mg per ml of the guaifenesin tannate. Each ml of the injectable liquid typically would additionally contain about 25 to 100 mg dextrose (anhydrous), about 10 to about 40 mg propylene glycol, about 5 to about 20 mg of dimethylacetamide (parental grade), about 0.25 to 1 g of edetate disodium and water for injection q.s.

If desired, the guaifenesin tannate composition of the invention may be formulated with other pharmaceutically active ingredients such as antihistamines and antitussives, e.g., chlorpheniramine, brompheniramine, pyrilamine, phenylephrine, ephedrine, pseudoephedrine, dextromethorphan, carbetapentane, carbinoxamine, and the like. Typically, these other active ingredients will be employed in the form of their free bases or their salts, e.g., citrates, maleates, hydrobromides, hydrochlorides, tannates, etc.

Of course, the dosage of the guaifenesin tannate of the present invention, alone or in combination with other pharmaceutically active ingredients to be administered will be dependent on the age, health and weight of the recipient, types of concurrent treatment, if any, frequency of treatment and effect desired.

The following nonlimiting examples shall serve to illustrate the present invention. Unless otherwise indicated, all parts and percentages are on a weight basis.

EXAMPLE 1

A 500 ml flask was equipped with a stirrer, thermometer, nitrogen blanket and a hot water bath. The hot water bath was heated to, and maintained at, a temperature of 85 to 90° C. Guaifenesin, USP grade, in the amount of 66 g (0.333 m) was placed in the flask, with slow stirring and allowed to become completely molten. Thereafter, the water bath temperature was raised to 90 to 100° C. and tannic acid in the amount of 113.2 g (0.0666 m) was slowly added, over a period of fifteen minutes, to the molten guaifenesin, while stirring. The reaction mass was thereafter continued to be slowly stirred over a period of about one hour. Thereafter, stirring was discontinued and the reaction mixture was allowed to cool to room temperature. It was noticed that the tan-colored reaction mass became hard after about fifteen minutes at room temperature. The softening point of the material was determined to be in the range of 57 to 62° C.

The reaction mass was ground into a fine powder with a mortar and pestle. The yield of the product was 169.5 g (97.8% of theory on an anhydrous basis). Analysis of this material by FTIR spectroscopy showed the following: no peaks present at 2350 $cm^{-1}$, moderately-sized sharp peaks at 1700 and 1600 $cm^{-1}$, a large sharp peak at 1500 $cm^{-1}$, moderately-sized sharp peaks at 1425 and 1325 $cm^{-1}$, a large sharp peak at 1025 $cm^{-1}$ and a very large sharp peak at 745 $cm^{-1}$.

By way of contrast, analysis of tannic acid by FTIR spectroscopy showed the following peaks: a short, broad peak extending from 3400 to 3100 $cm^{-1}$, a moderately-sized sharp peak at 2350 $cm^{-1}$, moderately-sized sharp peaks at 1700 and 1600 $cm^{-1}$, no peak at 1500 $cm^{-1}$, a very large sharp peak at 1175 $cm^{-1}$, a large sharp peak at 1025 $cm^{-1}$ and a moderately-sized peak at 750 $cm^{-1}$.

Analysis of guaifenesin by FTIR spectroscopy showed the following peaks: a small-sized peak at 3250 $cm^{-1}$, a very short peak at 2400 $cm^{-1}$, a small-sized peak at 1600 $cm^{-1}$, a large sharp peak at 1500 $cm^{-1}$, a moderately-sized sharp peak at 1450 $cm^{-1}$, short, sharp peaks at 1400, 1350 and 1300 $cm^{-1}$, large-sized, sharp peaks at 1250 and 1200 $cm^{-1}$, a short, sharp peak at 1175 $cm^{-1}$, large-sized sharp peaks at 1100 and 1075 $cm^{-1}$, large-sized sharp peaks at 1050, 1025 and 1000 $cm^{-1}$, moderate-sized peaks at 950, 900 and 850 $cm^{-1}$, a large-sized sharp peak at 775 $cm^{-1}$ and a very large-sized sharp peak at 750 $cm^{-1}$.

EXAMPLE 2

In order to determine whether the guaifenesin tannate was merely a synthetic mixture of guaifenesin and tannic acid, 66 g (0.333 m) of guaifenesin USP were thoroughly mixed with 113.2 g (0.0666 m) of tannic acid and milled into a fine powder with a mortar and pestle. Analysis of the mixture by FTIR spectroscopy showed that it had the same spectral pattern as that of tannic acid described above (it appears that the spectral pattern of tannic acid suppresses the spectral pattern of guaifenesin). The softening point of the synthetic mixture was determined to be in the range of 75 to 80° C.

Two grams of the synthetic mixture were placed in a beaker and 110 g of methylene chloride were added and the mixture was vigorously stirred with a magnetic stirrer for ten minutes. Methylene chloride was chosen for this experiment since it is a very good solvent for guaifenesin, but tannic acid is insoluble in methylene chloride.

The contents of the beaker were filtered through filter paper and the tan-colored precipitate was dried. The weight of the precipitate was 1.210 g, the exact amount of the tannic acid in the two gram aliquot portion of the synthetic mixture. Analysis of the tan-colored powder by FTIR spectroscopy confirmed that the material was tannic acid.

The filtrate was evaporated to dryness in an evaporating dish and 0.740 g of a white powder were recovered. The amount of 0.740 g represents the exact amount of the guaifenesin in the two gram aliquot portion of the synthetic mixture. Analysis of the white powder by FTIR spectroscopy confirmed that the material was guaifenesin.

EXAMPLE 3

Example 2 was repeated using a two gram aliquot portion of the material prepared in Example 1. The precipitate, after drying, weighed 1.95 g, substantially the same amount of the two gram aliquot portion. FTIR spectroscopy confirmed that the precipitate was neither guaifenesin nor tannic acid. The filtrate was evaporated to dryness and yielded 0.007 g of a white powder which was most likely unreacted guaifenesin.

The results obtained in Examples 2 and 3 clearly indicate that when tannic acid is added to guaifenesin in the molten state in accordance with the procedure set forth in Example 1, a new composition of matter results which is neither guaifenesin nor tannic acid. Such new composition of matter is clearly not a physical mixture of guaifenesin and tannic acid, but appears to be a composition in the form or a complex.

What is claimed is:

1. A composition comprising guaifenesin tannate.

2. A therapeutic expectorant composition for promoting or facilitating the removal of secretions from the respiratory tract in a warm-blooded animal comprising a pharmaceutically effective amount of an active ingredient comprising guaifenesin tannate.

3. A therapeutic composition as claimed in claim 2 in tablet form.

4. A therapeutic composition as claimed in claim 2 in suspension form.

5. A therapeutic composition as claimed in claim 2 further comprising one or more antitussive and/or antihistamine compositions.

6. The composition of claim 5 wherein the antitussive and/or antihistamine compositions are selected from the group consisting of chlorpheniramine, brompheniramine, pyrilamine, phenylephrine, ephedrine, pseudoephedrine, dextromethorphan, carbetapentane and carbinoxamine.

7. A method as claimed in claim 5 wherein said composition is in tablet form.

8. A method as claimed in claim 5 wherein said composition is in suspension form.

9. A central nervous system muscle relaxant composition for non-human warm-blooded animals comprising a pharmaceutically effective amount of an active ingredient comprising guaifenesin tannate.

10. The composition of claim 9 wherein said composition is in injectable form.

\* \* \* \* \*